(12) United States Patent
Prince

(10) Patent No.: US 11,369,782 B2
(45) Date of Patent: Jun. 28, 2022

(54) METHODS FOR ADMINISTERING MULTIPLE ALLERGENS

(71) Applicant: Ty L. Prince, Knoxville, TN (US)

(72) Inventor: Ty L. Prince, Knoxville, TN (US)

( * ) Notice: Subject to any disclaimer, the term of this patent is extended or adjusted under 35 U.S.C. 154(b) by 0 days.

(21) Appl. No.: 17/468,132

(22) Filed: Sep. 7, 2021

(65) Prior Publication Data

US 2022/0126078 A1 Apr. 28, 2022

Related U.S. Application Data

(63) Continuation-in-part of application No. 17/402,413, filed on Aug. 13, 2021.

(60) Provisional application No. 63/177,515, filed on Apr. 21, 2021, provisional application No. 63/171,995, filed on Apr. 7, 2021, provisional application No. 63/106,793, filed on Oct. 28, 2020.

(51) Int. Cl.
*A61M 37/00* (2006.01)

(52) U.S. Cl.
CPC ....... *A61M 37/00* (2013.01); *A61M 2209/045* (2013.01); *A61M 2210/04* (2013.01)

(58) Field of Classification Search
CPC ............ A61M 37/00; A61M 2209/045; A61M 2210/04; A61B 17/205; A61B 10/0035; A61B 5/411; A61B 17/32093; A61B 50/22
USPC ........... 600/556; 604/46; D24/147; 422/430; 424/9.81
See application file for complete search history.

(56) References Cited

U.S. PATENT DOCUMENTS

| | | | |
|---|---|---|---|
| 5,551,441 A * | 9/1996 | Pitesky ................ | A61B 17/205 600/556 |
| 5,671,753 A * | 9/1997 | Pitesky ................ | A61B 17/205 600/556 |
| 5,871,452 A * | 2/1999 | Baker .................... | A61B 5/411 600/556 |
| 5,931,794 A | 8/1999 | Pitesky | |
| 6,206,838 B1 * | 3/2001 | Doll ..................... | A61B 17/205 600/556 |
| 6,554,777 B1 | 4/2003 | Hein, Jr. | |
| 7,186,235 B2 * | 3/2007 | Martin ................. | A61B 17/205 604/185 |
| 9,597,030 B2 | 3/2017 | Smollar | |
| 2006/0178615 A1 | 8/2006 | Ronborg et al. | |

(Continued)

*Primary Examiner* — Alex M Valvis
*Assistant Examiner* — Chanel J Jhin
(74) *Attorney, Agent, or Firm* — Gerald R. Black, Esq.

(57) ABSTRACT

The method for administering a plurality of allergens into the skin of a patient uses a multiple test applicator in cooperative engagement with a fluid tray. The applicator has a plurality of scratching barbs each aligned with a plurality of reservoirs in the fluid tray. The method deploys allergen loading followed by allergen deposition. During allergen loading, a different allergen is loaded onto each respective scratching barb from each respective reservoir. Each scratching barb is designed to retain a trace amount of allergen. The applicator fits into one hand of a medical technician administering the skin test. The applicator is removed from the fluid tray and repositioned onto the skin of the patient for allergen deposition. Then, each scratching barb pierces the outer layer of the skin at each respective test site as a trace amount of each respective allergen seeps into each respective test site from each scratching barb.

28 Claims, 13 Drawing Sheets

DETAIL "A"
ALLERGEN LOADING

(56) References Cited

U.S. PATENT DOCUMENTS

2009/0118638 A1 5/2009 Schindlbeck et al.
2017/0281158 A1* 10/2017 Lear .................. A61B 17/0644

* cited by examiner

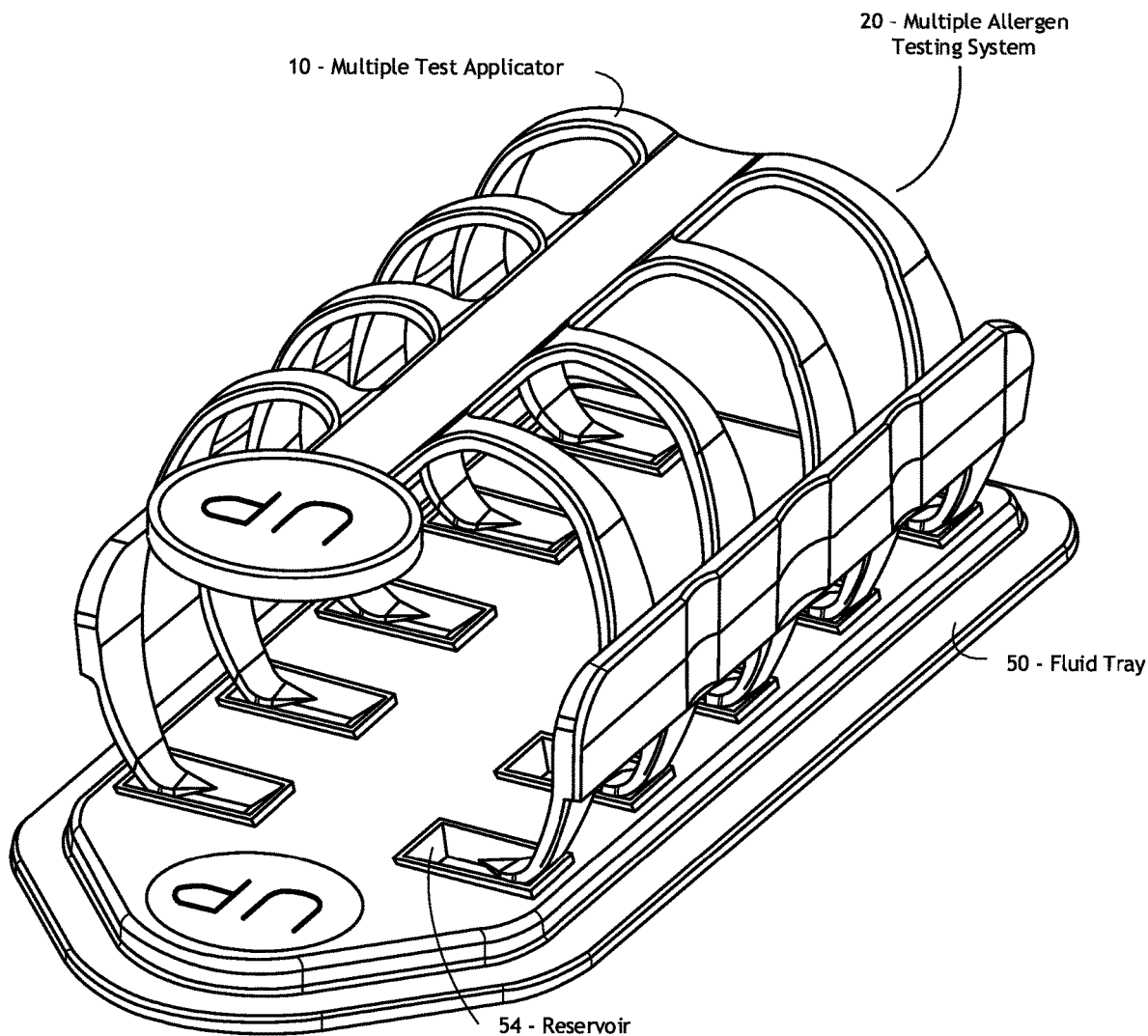
FIGURE 1
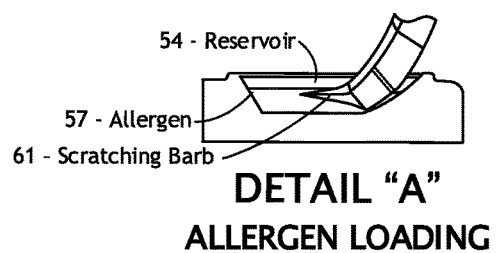
DETAIL "A"
ALLERGEN LOADING

ALLERGEN DEPOSITION

RELAXED STATE

COMPRESSED STATE

COMPRESSED STATE

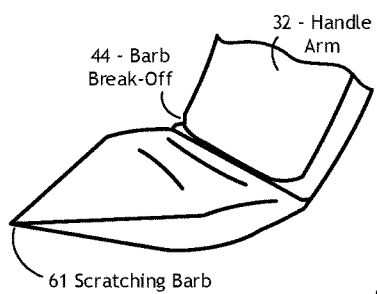 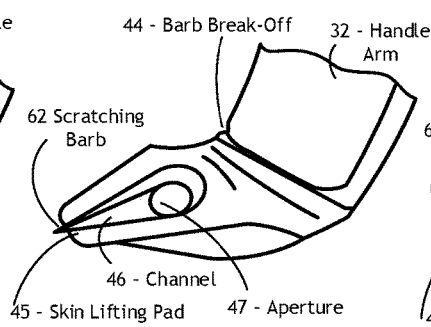 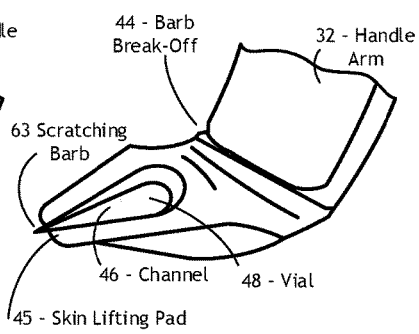
FIGURE 7A
BARB TILTED UP
FIGURE 7B
BARB TILTED UP
FIGURE 7C
BARB TILTED UP

DETAIL "B"
ALLERGEN LOADING

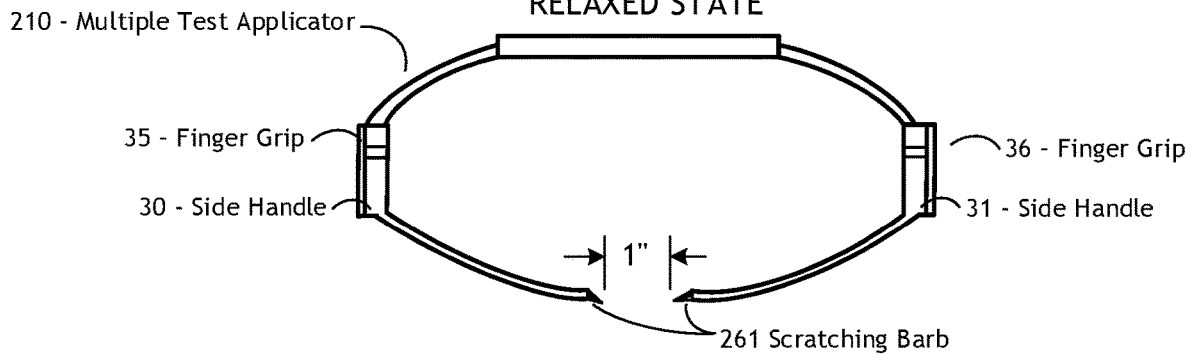
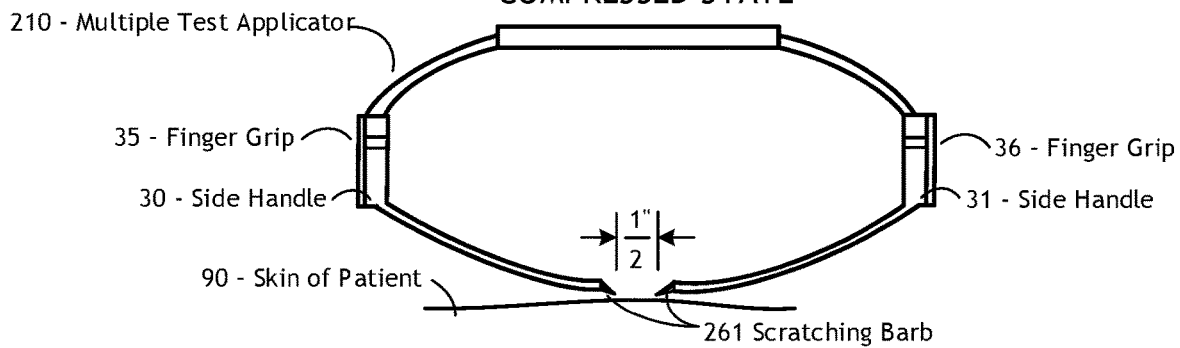
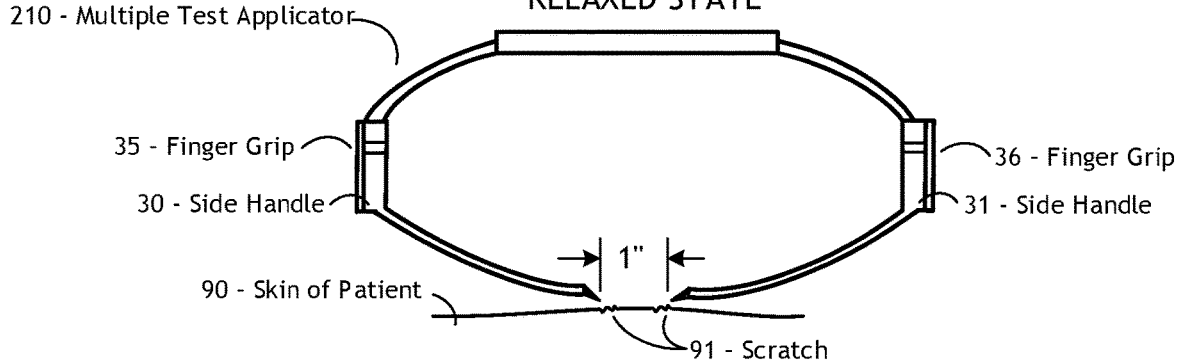

BARB TILTED DOWN

BARB TILTED DOWN

BARB TILTED DOWN

METHODS FOR ADMINISTERING MULTIPLE ALLERGENS

CROSS-REFERENCE TO RELATED APPLICATIONS

This application is a continuation-in-part to and claims priority to U.S. patent application Ser. No. 17/402,413, entitled "Multiple Allergen Test Applicator" (Prince), filed on Aug. 13, 2021; U.S. Provisional Application No. 63/177, 515, entitled "Single and Multiple Allergen Testing System" (Prince), filed on Apr. 21, 2021; U.S. Provisional Application No. 63/171,995, entitled "Penicillin Allergy Test Kit" (Prince and Novak), filed on Apr. 7, 2021; U.S. Provisional Application No. 63/142,150, entitled "Sharps Disposal System" (Prince and Novak), filed on Jan. 27, 2021; U.S. Provisional Application No. 63/124,943 entitled "Automated Allergy Office" (Prince) filed: on Dec. 14, 2020; and U.S. Provisional Application No. 63/106,793, entitled "Single and Multiple Allergen Skin Testing System" (Prince) filed on Oct. 28, 2020.

FIELD OF USE

The present invention relates to new methods for administering multiple allergens into the skin of a patient, and more particularly, to methods for conducting multiple allergy scratch tests.

BACKGROUND OF THE INVENTION

There is an increasing population of allergy disease sufferers. Accordingly, there is a growing need to identify these people and their allergy issues, and to reduce this suffering.

The medical technician administering these skin tests may often need to apply a relatively large number of different allergens to the skin of a patient. To perform skin tests of this type, the medical technician removes the skin-test device with a small amount of allergen deposited on the sharp pointed testing tips and applies the allergen to the patient in a predetermined sequence.

Some skin testing methods known to treat patients include:

U.S. Pat. No. 6,554,777 (Hein, Jr.) discloses a multi-site skin-test system. The system includes a reservoir tray and strips of interconnected reservoir caps inserted into upper portions of the reservoirs. The caps each include a generally conically shaped hole. Connection members connect the caps of a strip to one another. The strips of caps are pressed into tightly fitting upper portions of reservoirs having upwardly facing ledge surfaces for supporting downwardly facing bottom surfaces of the caps. The outer side surfaces of the caps and the inner surfaces of the upper portions of the reservoirs are substantially the same size to provide a tight fit. A tray lid includes a downwardly extending ridge that cooperates with the tray to prevent the lid from being placed onto the tray backwards.

U.S. Pat. No. 9,597,030 (Smollar) depicts an allergy testing kit containing a plurality of allergy testing applicators, an allergy testing tray, and a plurality of allergen bottles each containing an allergen. Each of the applicators contains an elongated handle, a plurality of arms extending from the elongated handle and disposed in an asymmetrical configuration, and a plurality of legs with tines extending from each of the arms. The allergy testing tray contains a main body having an underside and a top surface, a cover for locking with the main body and a plurality of reservoirs extending from the underside of the main body. The reservoirs each have a chamber with an opening extending from the top surface. The reservoirs are disposed in different groups and each group has an asymmetrical configuration matching that of the applicator.

U.S. patent application Ser. No. 11/885,086 (Schindlbeck; et al.) depicts a device for performing an allergy test. The device comprises a container assembly including several containers designed to receive the allergens, and a mark transferable onto the skin which is used to associate specific allergens to specific allergy sites on the skin of a living being undergoing an allergy test. The device aims at improving so that the allergy test sites on the skin can be constantly marked very legibly, and so that the corresponding marks can be readily eliminated from the skin immediately after the allergy test.

U.S. patent application Ser. No. 10/558,943 (Ronborg; et al.) discloses an allergy tester for delivering a diagnostic agent to the skin or mucosa of a patient. A chamber filled with the diagnostic agent is separate from the housing with a rod capable of transferring the diagnostic agent to the animal. The chamber is connected to the housing with the rod before transfer of diagnostic agent. In particular, the invention relates to a device for delivering allergens in allergy tests.

Oftentimes, many different allergens need to be screened for a particular patient. Hence, it becomes necessary to minimize patient discomfort while accumulating patient data so that the proper course of treatment can be identified.

What is needed are methods for administering multiple allergens that will replace needle pricks that are commonly used: a simple, economical, and reliable scratch testing method in which multiple allergens can be tested simultaneously on the skin of a patient which minimizes any cross contamination of allergens, that simplifies the handling of the applicator device and provides results that are easily observable.

What is needed are methods that significantly reduce the possibility of errors in reading the test results while reducing false positives, and minimizing patient discomfort, that is cost-effective, and is easy to use and manufacture.

Certain other objects and advantages of the invention will become apparent from the following description of preferred embodiments of the invention taken in connection with the accompanying drawings.

SUMMARY OF THE INVENTION

The methods for administering multiple allergens of the present invention addresses these needs.

The method for administering a plurality of allergens into skin of a patient uses a multiple skin test system.

The multiple allergen testing system is removed from its sterile package. The multiple skin test system includes a multiple test applicator that is in cooperative engagement with a fluid tray. The multiple test applicator has a relaxed state and a compressed state.

The method for administering a plurality of allergens into skin of a patient is a two-stage process: (1) allergen loading, and (2) allergen deposition.

The multiple test applicator includes a pair of opposing side frames. Each side frame opposing includes a first finger grip. The multiple test applicator is preferably sized to be held in one hand of a medical technician administering the allergen skin testing. A pair of finger grips are positioned on opposing sides of the applicator frame. The medical technician grasps the applicator by the pair of opposing finger grips in her hand during allergen loading and allergen deposition to change the multiple test applicator from the compressed state to the relaxed state, and back again. During allergen loading, the multiple test applicator is in the relaxed state.

The method comprises a medical technician using one hand positioning a multiple test applicator onto a loading tray during allergen loading.

The multiple test applicator includes multiple scratching barbs. Each scratching barb is positioned in a reservoir containing an allergen fluid during allergen loading.

Preferably, each of the scratching barbs of the multiple test applicator project upward toward the spine of the applicator when disposed in the fluid tray. Each scratching barb is sandwiched between a pair of skin lifting pads. When placed upon the skin of the patient during allergen deposition, the multiple test applicator is repositioned from the relaxed state to the compressed state raising the skin between the opposing rows of scratching barbs, the multi tester is then pulled up generating the plurality of scratches into the epidermis of the patient and injecting trace amounts of each respective allergen into each respective scratch.

In the preferred embodiment of the method for administering multiple allergens of the present invention, each scratching barb of the multiple test applicator projects upward away from the fluid tray when positioned in the fluid tray. The fluid tray contains multiple allergens, generally one allergen in each reservoir. Allergens are initially selected and placed into containment reservoirs in the fluid tray, and care is taken not to use an excess amount of the allergens. When subsequently repositioned upon the skin of the patient, the scratching barbs contact both sides of the raised portion of the skin of the patient. The skin of the patient is raised by the skin lifting pads on each side of each scratching barb. Also, the skin lifting pads are positioned relative to each scratching barb to limit the depth that each scratching barb penetrates the skin of the patient. The multiple test applicator generates a scratch at each test site as the medical technician manipulates the multiple test applicator upward or downward, as trace amounts of each respective allergen seep into each respective scratch at each test site. The use of the finger grips to move the multiple test applicator from the relaxed state to the compressed state and then back again to the relaxed state enables one-handed operation by the medical technician. Then, the multiple test applicator is pulled up and away from the skin of the patient. The medical technician then waits between 10 to 20 minutes to determine how the patient has reacted to each of these allergens. After the testing has been completed, the physician analyzes the test results to determine the next course of treatment.

In an alternate embodiment of the method for administering multiple allergens of the present invention, each of the scratching barbs of the multiple test applicator points downward toward the fluid tray when disposed in the fluid tray. The fluid tray contains multiple allergens, generally one allergen in each reservoir. Allergens are initially selected and placed into containment reservoirs in the fluid tray, and care is taken not to use an excess amount of the allergens. After allergen loading when the medical technician lifts the multiple test applicator out of the fluid tray, the multiple test applicator is in the relaxed state. Using the pair of opposing finger grips, the medical technician applies pressure moving the multiple test applicator to a compressed state before placing the applicator upon the skin of the patient in the allergen deposition position, the medical technician pushes lightly upon the applicator and slowly releases the finger grips. This generates a scratch at each test site on the skin of the patient. Trace amounts of each respective allergen then seep into each respective scratch. The use of the finger grips to move the multiple test applicator from the relaxed state to the compressed state and then back again to the relaxed state enables one-handed operation by the medical technician. Then, the multiple test applicator is pulled up and away from the skin of the patient. The medical technician then waits between 10 to 20 minutes to determine how the patient has reacted to each of these allergens. After the testing has been completed, the physician analyzes the test results to determine the next course of treatment.

For allergies to initially develop, the body must be exposed to an allergen, that prompts the body to initiate an immune response.

In intradermal skin testing, a medical professional injects a tiny amount of allergen between the epidermis and the dermis of the patient. The immediate positive skin reaction reaches a peak in about fifteen minutes, and is a pale central area surrounded by redness (a flare) and a bump or swelling (a wheal).

In addition to the allergens in question, skin testing is also performed with a positive control (histamine) that should always cause a skin reaction, and a negative control (saline), that should not cause a reaction. A test is positive if the allergen causes a wheal 3 mm greater than the negative control, and if the skin has a response to the histamine, as well.

The allergic reaction is measured immediately after the application of the allergen. The information is a direct measure of the allergy reaction occurring under the skin. The information on each site is presented to the physician to compare against visual observations. A determination of the patient susceptibility to each allergen is determined by the physician and a course of future action is planned. A positive skin test does not predict the severity of an allergic reaction. A negative skin test usually means the patient is not allergic.

In general, allergy skin tests are reliable for diagnosing allergies to airborne substances, such as pollen, pet dander and dust mites. Skin testing may help diagnose food allergies, but because food allergies can be complex, additional procedures may be required.

The multiple test applicator and fluid tray are designed to minimize any cross contamination of the various allergens.

For a complete understanding of the methods for administering multiple allergens, reference is made to the accompanying drawings and description in which the presently preferred embodiments of the invention are shown by way of example. As the invention may be embodied in many forms without departing from spirit of essential characteristics thereof, it is expressly understood that the drawings are for purposes of illustration and description only and are not intended as a definition of the limits of the invention.

BRIEF DESCRIPTION OF THE DRAWINGS

FIG. 1 depicts an assembly view of a first preferred embodiment of an allergy testing system comprising a first preferred embodiment of the multiple test applicator having ten applicators cooperatively engaged with a fluid tray, the multiple test applicator being disposed on the fluid tray; and DETAIL "A" depicts an exploded side view of the scratching barb positioned in a reservoir of the fluid tray during allergen loading, the reservoir being partially filled with allergen.

FIG. 7A is an exploded assembly view of the first preferred embodiment of the scratching barb pointed upward toward the spine of the multiple test applicator of FIG. 1, a tip break-off section is also depicted.

FIG. 7B is an exploded assembly view of a second preferred embodiment of the scratching barb pointed upward toward the spine of the multiple test applicator of FIG. 1, the scratching barb including an aperture and a channel for retaining a trace amount of the allergen, a tip break-off section is also depicted. Skin lifting pads are shown on both sides of the barb, they lift the skin and limit the depth of the scratching barb.

FIG. 7C is an exploded assembly view of a third preferred embodiment of the scratching barb pointed upward toward the spine of the multiple test applicator of FIG. 1, the scratching barb including a vial and a channel for retaining a trace amount of the allergen, a tip break-off section is also depicted. Skin lifting pads are shown on both sides of the barb, they lift the skin and limit the depth of the scratching barb.

FIG. 13A is a front view of the multiple test applicator [210] in an expanded position, with the scratching barbs, the scratching barbs now being loaded, and each include a trace of their respective allergens and are prepared for allergen deposition.

FIG. 13B is a front view of the multiple test applicator of FIG. 13A, the multiple test applicator now being in a compressed position. The scratching barbs are resting upon the skin of a patient with the each of two scratching barbs pointed downward.

FIG. 13C is a front view of the multiple test applicator of FIG. 13B, the multiple test applicator now being in an expanded position, the scratching barbs now have generated a pair of scratches at a pair of test sites as the scratching barbs move away from each other.

DETAILED DESCRIPTION OF THE PREFERRED EMBODIMENTS

Figure 2:
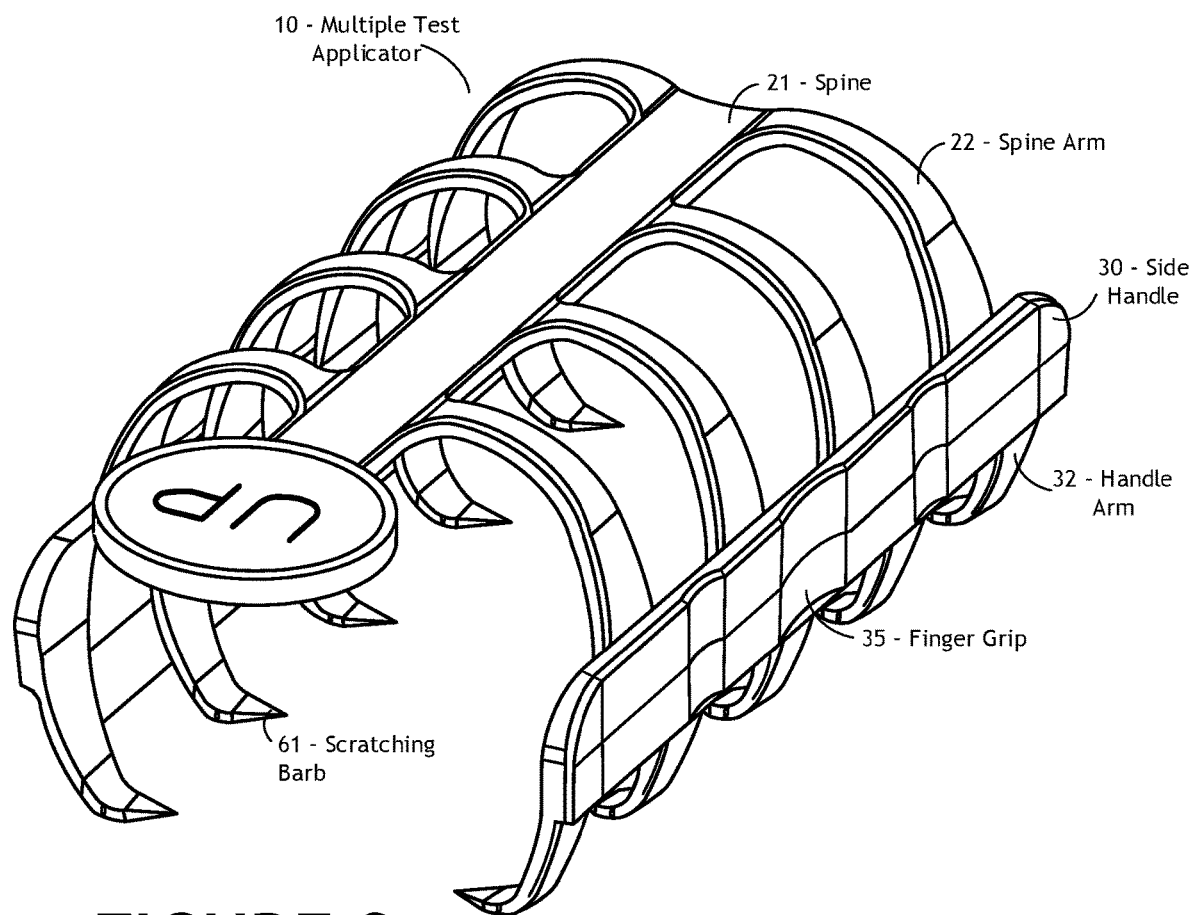
FIG. 2 depicts the first preferred embodiment of the multiple test applicator as shown in FIG. 1.

Referring now to the drawings, FIG. 1 depicts an assembly view of a first preferred embodiment of an allergy testing system [20] comprising of a first preferred embodiment of the multiple test applicator [10] having ten applicators cooperatively engaged with a fluid tray [50]. The multiple test applicator [10] is cooperatively engageable with the ten allergen reservoirs [54], each one retaining a different liquid for allergen skin testing.

The multiple test applicator [10] has an allergen loading position and an allergen deposition position.

DETAIL "A" depicts an exploded side view of a scratching barb [61] positioned in a reservoir [54] of the fluid tray [50] during allergen loading. The reservoir [50] is partially filled with allergen [57]. During allergen loading, the scratching barbs [61] are dipped into the allergen [57] setting in the reservoirs [54].

FIG. 2 depicts the first preferred embodiment of the multiple test applicator [10] as shown in FIG. 1. Each of the ten scratching barbs [61] is cooperatively engageable with one of the ten reservoirs [54] of the fluid tray [50] and has a slight upward tilt.

The multiple test applicator is made of compressible material. The materials of choice are engineering grade polymers, since the multiple test applicator needs to be sterilized in an autoclave prior to use, the material must be stable at elevated temperatures.

The preferred embodiment of the method for administering multiple allergens into the skin of a patient [90] uses a multiple skin test system [20]. The multiple allergen testing system [20] is removed from its sterile package. The multiple skin test system [20] includes a multiple test applicator [10] that is in cooperative engagement with a fluid tray [10]. The multiple test applicator [10] has a relaxed state and a compressed state.

The method for administering a plurality of allergens into skin of a patient is a two-stage process: (1) allergen loading, and (2) allergen deposition.

During allergen loading, the multiple test applicator [10] is in the relaxed state.

The multiple test applicator [10] a pair of opposing side frames [30 and 31]. Each opposing side frame [30 and 31] includes a first finger grip [35 and 36]. The multiple test applicator [10] is preferably sized to be held in one hand of a medical technician administering the allergen skin testing. A pair of finger grips [35 and 36] are positioned on opposing sides of each opposing applicator frame [30 and 31]. The medical technician grasps the applicator [10] by the pair of opposing finger grips [35 and 36] in her hand during allergen loading and allergen deposition.

The method involves one hand of a medical technician [96] positioning a multiple test applicator [10] onto a loading tray [50] during allergen loading.

The fluid tray has [50] multiple allergens retainable in multiple reservoirs [54]. Allergens are initially selected and placed into the individual containment reservoirs [54] in the fluid tray [50], and care is taken not to use an excess amount of the allergens.

The multiple test applicator has multiple scratching barbs [61]. During allergen loading each scratching barb is positioned in a reservoir [54] containing an allergen [57].

The method for administering a plurality of allergens into skin of a patient [90] then uses the same hand of the medical technician [96] to relocate the multiple test applicator [10] onto the skin of the patient [90] during allergen deposition.

With the scratching barbs [61] now positioned on the skin of the patient [90], the multiple test applicator [10] is moved from the relaxed state to the compressed state.

In so doing, the scratching barbs [61] will break the skin of the patient [90] and generate a plurality of small scratches [91]. A trace amount of each allergen [57] has been retained on each scratching barb [61] and is inserted into each scratch [91], respectively.

Allergens [57] are placed into respective reservoirs [54] in the fluid tray [50]. Care is taken to avoid using excess amounts of allergens [57] which may cause cross contamination of allergens.

The size of the reservoirs [54] and the distance between adjacent reservoirs [54] are designed to minimize any cross contamination of the allergens [57].

In the allergen loading position, a different scratching barb [61] is positioned into each respective reservoir [54] of the loading tray [50]. Each scratching barb [61] contacts a small amount of the allergen [57] in each respective reservoir [54]. Each scratching barb [61] retains a trace amount of allergen [57] in the allergen loading position which is deposited under the dermis and above the epidermis of the patient in the allergen deposition position.

Figure 3:
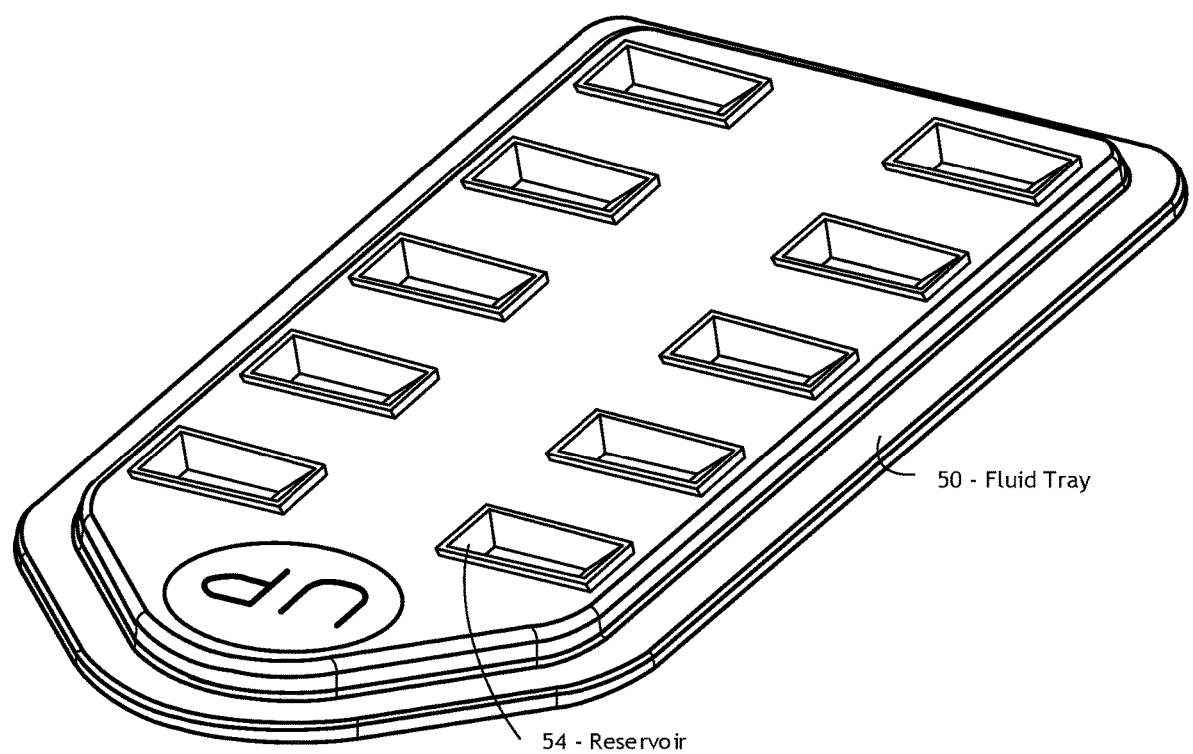
FIG. 3 depicts a detailed assembly view of the fluid tray of FIG. 1 complete with ten reservoirs.

FIG. 3 depicts a detailed assembly view of the fluid tray [50] complete with ten reservoirs [54].

Figure 4:
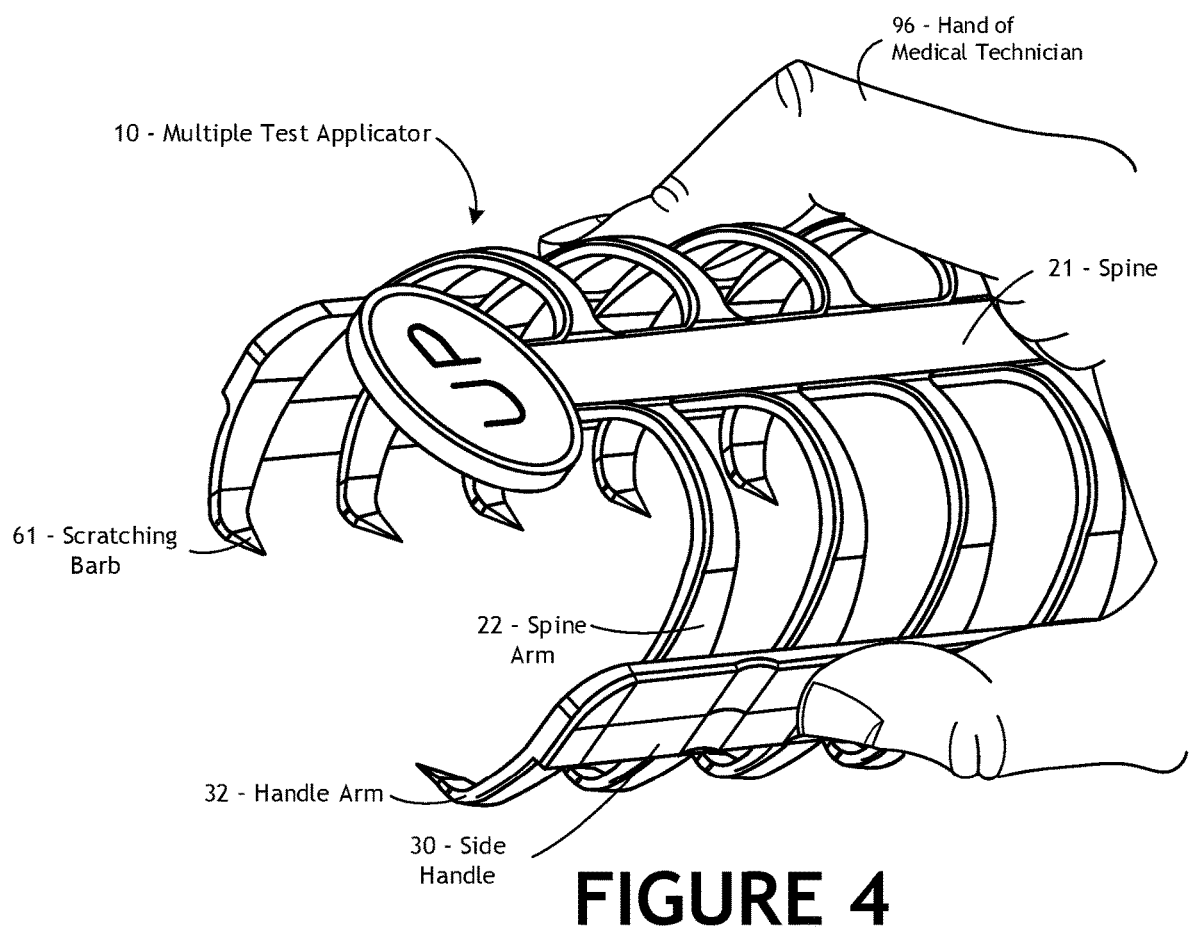
FIG. 4 depicts the first preferred embodiment of the multiple test applicator of FIG. 2 held in one hand of a medical technician, with the thumb positioned on a first finger grip on a first side frame and the index finger positioned on a second finger grip on a second side frame, the first side frame opposing the second side frame.

FIG. 4 depicts the first preferred embodiment of the multiple test applicator [10] of FIG. 2 held in one hand of a medical technician, with the thumb positioned on a finger grip [35] on a first side handle [30] and the index finger positioned on a second finger grip [36] on a second side handle [31], the second side handle [31] opposing the first side handle [30]. The multiple test applicator [10] is preferably sized to be held in one hand of a medical technician administering the allergen skin testing.

It is critical that the multiple test applicator [10] be held in one hand of the medical technician who is administering the test. This enables the other hand to be free to take notes, to assist the patient, or do whatever becomes else necessary during the administration of the procedure.

Figure 5:
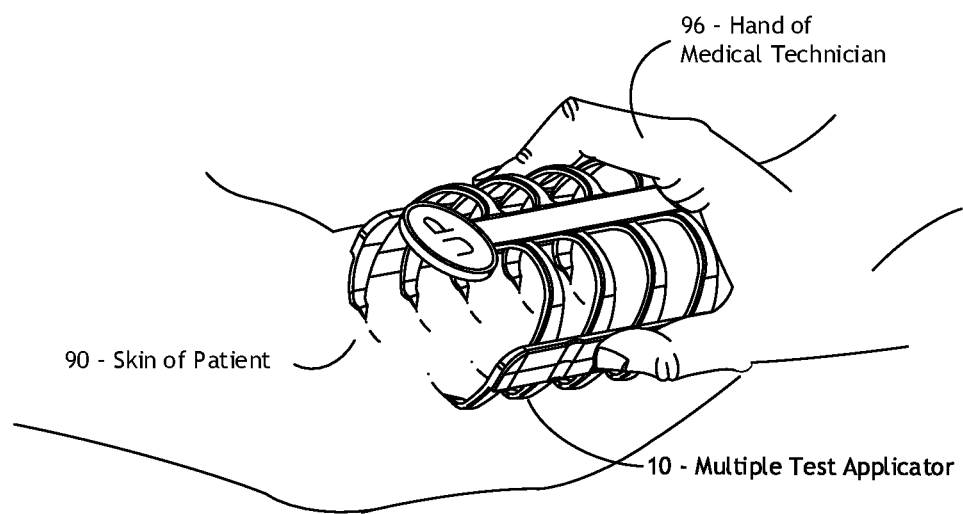
FIG. 5 depicts the first preferred embodiment of the multiple test applicator of FIG. 2 held in one hand of a medical technician as the allergens are deposited under the skin (forearm) of a patient.

FIG. 5 depicts the first preferred embodiment of the multiple test applicator [10] held in one hand of a medical technician [96] as the allergens are deposited under the skin (forearm) of a patient [90].

Figure 6A:
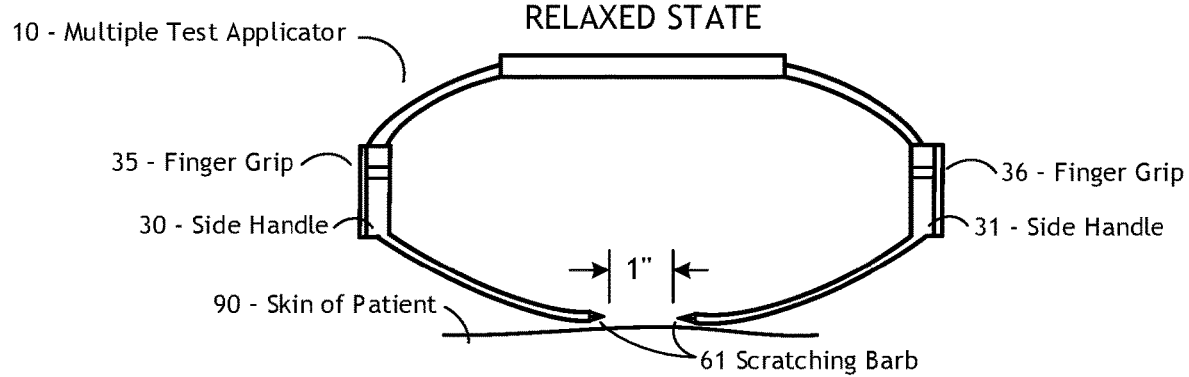
FIG. 6A is a front view of the multiple test applicator of FIG. 1, the multiple test applicator being in an expanded position, the scratching barbs resting upon the skin of a patient.
Figure 6B:
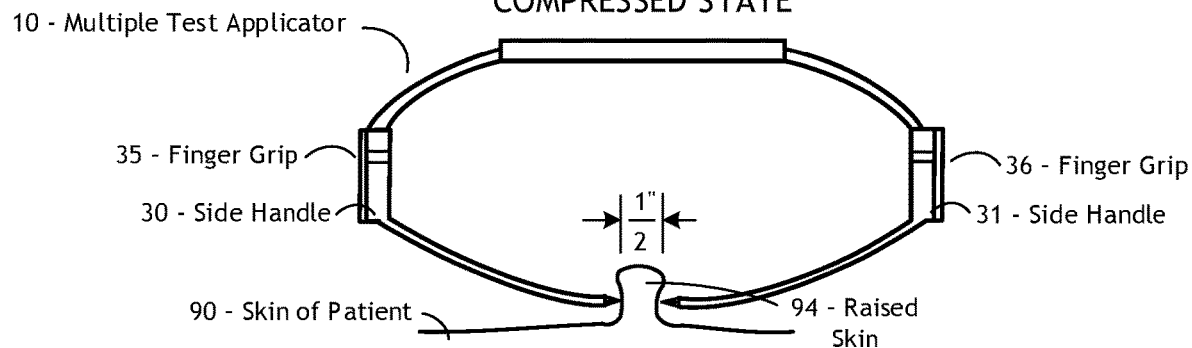
FIG. 6B is a front view of the multiple test applicator of FIG. 6A, the multiple test applicator now being in a compressed position, the scratching barbs resting upon the skin of a patient with each of the opposed scratching barbs disposed at two test sites of a patient, with the skin having been lifted upwards between the pair of opposed scratching barbs.
Figure 6C:
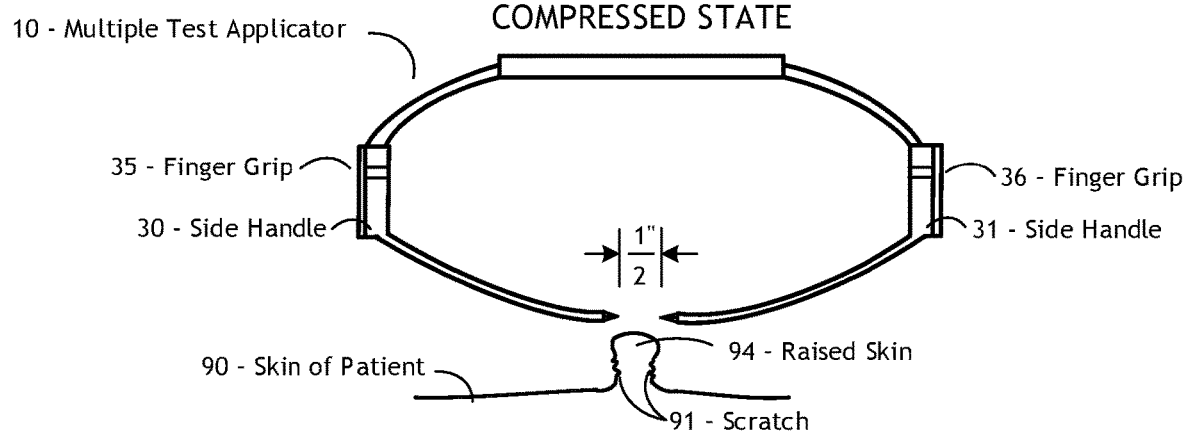
FIG. 6C is a front view of the multiple test applicator of FIG. 6B, the multiple test applicator still being in a compressed position, the scratching barbs now being raised from the skin of the patient with scratches now appearing on each side of the raised skin of the patient.

FIGS. 6A, 6B, and 6C depict the preferred embodiment of the method for administering multiple allergens of the present invention, each scratching barb [61] of the multiple test applicator [10] points upward away from the fluid tray [50] when positioned in the fluid tray [50]. The fluid tray [50] contains multiple allergens, generally one allergen [57] in each reservoir [54]. The allergens [57] are initially selected and placed into each containment reservoir [54] of the fluid tray [50], and care is taken not to use an excess amount of the allergens. When subsequently repositioned upon the skin of the patient [90], the scratching barbs [61] contact both sides of the raised portion of the skin [94] of the patient. The skin of the patient [90] is raised by the pair of skin lifting pads [45], one positioned on each side of each scratching barb [61]. Also, the skin lifting pads [45] are positioned relative to each scratching barb [61] to limit the depth that each scratching barb [61] penetrates the skin of the patient [90]. The multiple test applicator [10] generates a scratch [91] at each test site essentially simultaneously as the medical technician manipulates the multiple test applicator [10] upward or downward, as trace amounts of each respective allergen [57] seep into each respective scratch [91] at each test site. The use of the finger grips [35 and 36] to move the multiple test applicator [10] from the relaxed state to the compressed state and then back again to the relaxed state enables one-handed operation by the medical technician. Then, the multiple test applicator [10] is pulled up and away from the skin of the patient [90]. The medical technician then waits between 10 to 20 minutes to determine how the patient has reacted to each of these allergens [57]. After the testing has been completed, the physician analyzes the test results to determine the next course of treatment.

FIG. 6A is a front view of the multiple test applicator [10] in an expanded position, with the scratching barbs [61] resting upon the skin of a patient [90]. The scratching barbs [61] each include a trace amount of their respective allergens and are prepared for allergen deposition.

FIG. 6B is a front view of the multiple test applicator [10]. The multiple test applicator is now being in a compressed position by use of the pair of finger grips [35 and 36]. The scratching barbs [61] are resting upon the skin of the patient [90] with the each of two scratching barbs [61] disposed about a portion of the skin of a patient [90] that has been lifted upwards [94] between the pair of opposed scratching barbs [61]. The multiple test applicator [10] is in the allergen deposition position.

FIG. 6C is a front view of the multiple test applicator of FIG. 5B. The multiple test applicator [10] is still being compressed. The scratching barbs [61] now have been raised upward from the skin of the patient [90] with a pair of scratches [61] now appearing on each side of the portion of the skin of the patient that was lifted upwards [94].

Then, the multiple test applicator [10] is pulled up and away from the skin of the patient [90]. Then, the medical technician waits between 10 and 20 minutes to determine how the patient has reacted to these allergens. After the testing has been completed, the physician analyzes the test results to determine the next course of treatment.

FIG. 7A is an exploded assembly view of the first preferred embodiment of the scratching barb pointed upward [61] toward the spine [21] of the multiple test applicator [10]. A barb break-off section [45] is also shown.

FIG. 7B is an exploded assembly view of a second preferred embodiment of the scratching barb pointed upward [62] toward the spine [21] of the multiple test applicator [10]. The scratching barb [62] includes an aperture and a channel for retaining a trace amount of the respective allergen [57]. A barb break-off section [45] is also shown. A pair of skin lifting pads [45] are sandwiched about each scratching barb [61]. The pair of skin lifting pads [45] lift the skin and limit the depth of the scratching barb. The pair of skin lifting pads [45] control the depth of the penetration of the scratching barbs [61] and ensures repeatability of the testing.

FIG. 7C is an exploded assembly view of a third preferred embodiment of the scratching barb pointed upward [63] toward the spine [21] of the multiple test applicator [10]. The scratching barb includes a vial and a channel for retaining a trace amount of the respective allergen [57]. A barb break-off section [44] is also shown. A pair of skin lifting pads [45] are sandwiched about each scratching barb [61]. The pair of skin lifting pads [45] lift the skin and limit the depth of the scratching barb. The pair of skin lifting pads [45] control the depth of the penetration of the scratching barbs [61] and ensure repeatability of the testing.

Figure 8:
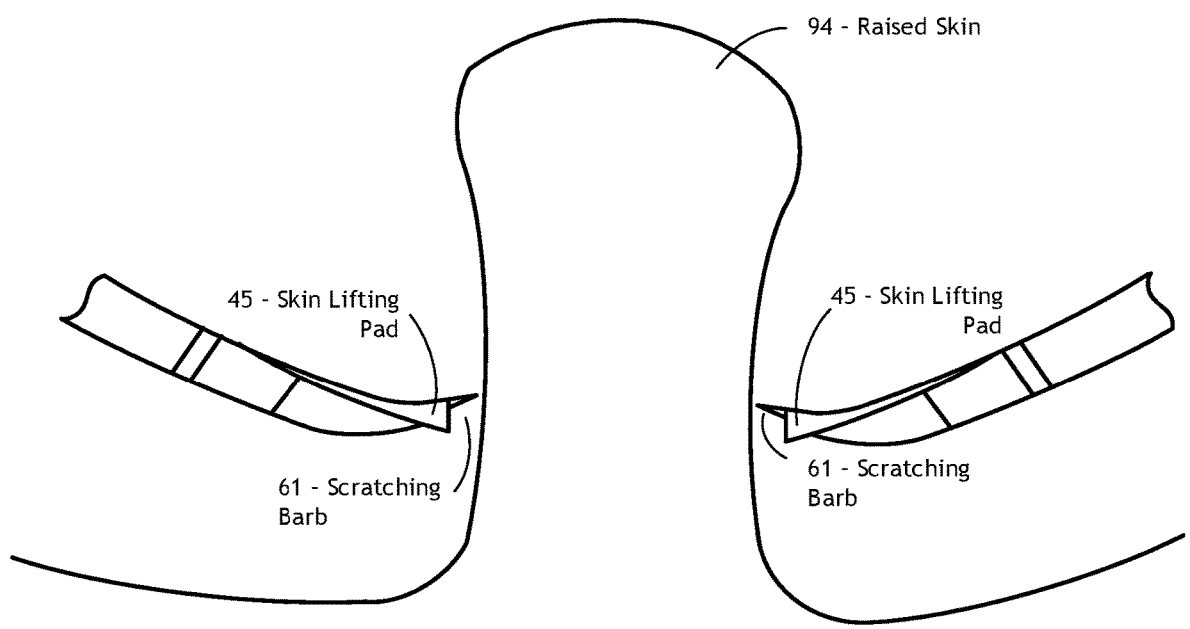
FIG. 8 depicts an exploded side view of a pair of scratching barbs being raised upward on a portion of the skin of a patient that has been pulled together to prepare the site for a pair of scratches from the pair of scratching barbs, a pair of skin lifting pads being positioned, one on each side of each skin scratching barb, that lift the skin and limit the depth of penetration of each scratching barb.

FIG. 8 depicts an exploded side view of a pair of scratching barbs [61] being raised upward on a portion of the skin of a patient that has been pulled together and raised [94] to prepare the site for a pair of scratches [91] from the pair of scratching barbs. Skin lifting pads [45] are shown on both sides of the barb, they lift the skin and limit the depth of the scratching barb.

Figure 9:
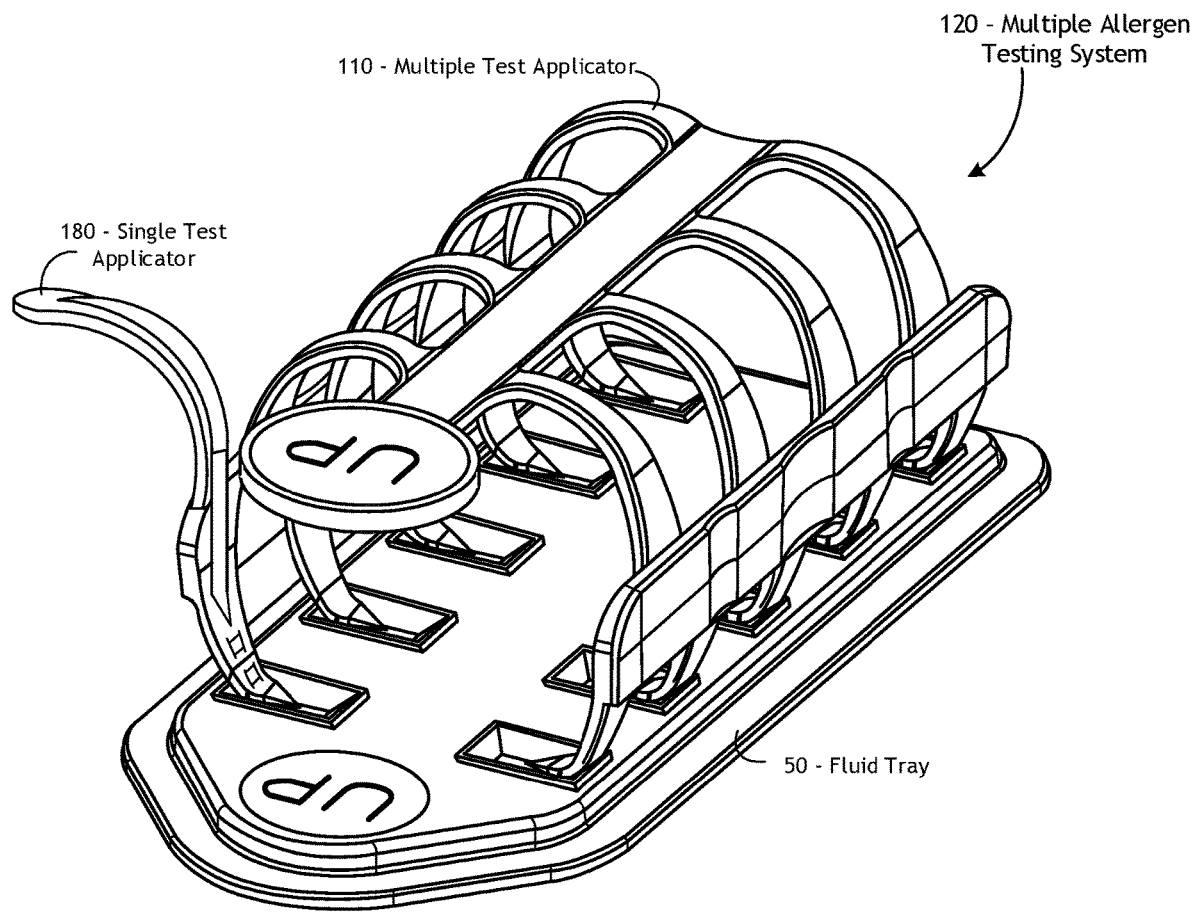
FIG. 9 depicts an assembly view of a second preferred embodiment of an allergy testing system comprising a second preferred embodiment of the multiple test applicator having nine scratching barbs, and a single test applicator with a single scratching barb, all being cooperatively engaged with ten fluid reservoirs in a fluid tray.

FIG. 9 depicts an assembly view of a second preferred embodiment of an allergy testing system [120] comprising a second preferred embodiment of the multiple test applicator [110] having nine scratching barbs, and a single test applicator [180] with a single scratching barb, all being cooperatively engaged with ten fluid reservoirs in a fluid tray [50]. The multiple test applicator is also compatible with multiple single test applicator units [180] when aligned with a fluid tray that is properly sized with the number and alignment of fluid reservoirs (not shown).

Figures 10A, 10B:
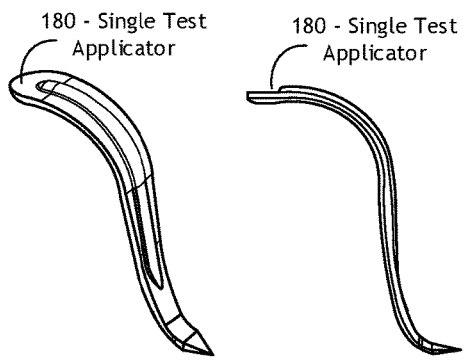
FIG. 10A depicts an assembly view of the single test applicator of FIG. 9.
FIG. 10B depicts an end view of the single test applicator of FIG. 10A.

FIG. 10A depicts an assembly view of the single test applicator [180] of FIG. 9, and FIG. 10B depicts an end view of the single test applicator [180] of FIG. 10A.

Figure 11:
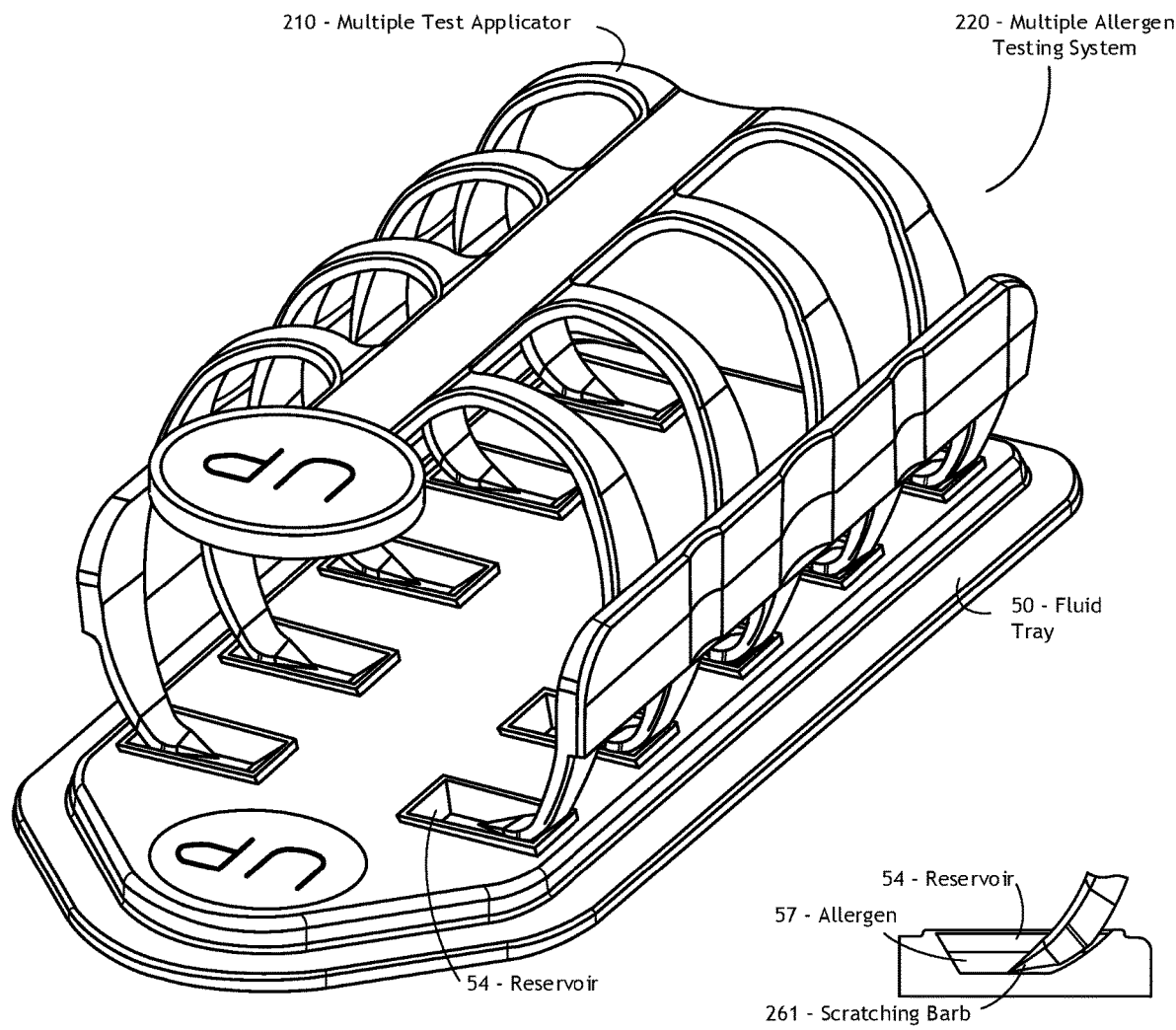
FIG. 11 depicts an assembly view of a third preferred embodiment of an allergy testing system comprising of a third preferred embodiment of the multiple test applicator having ten applicators cooperatively engaged with a fluid tray, the multiple test applicator being disposed on a fluid tray; and DETAIL "B" depicting an exploded side view of the scratching barb positioned in a reservoir of the fluid tray, the reservoir being partially filled with allergen.

FIG. 11 depicts an assembly view of a third preferred embodiment of an allergy testing system [220] comprising of a third preferred embodiment of the multiple test applicator [210] having ten applicators cooperatively engaged with a fluid tray [50].

DETAIL "B" depicts an exploded side view of the scratching barb [261] positioned in a reservoir [54] of the fluid tray [50] during allergen loading. The reservoir [54] is partially filled with allergen [57]. The scratching barbs [261] are pointed downward.

Figure 12:
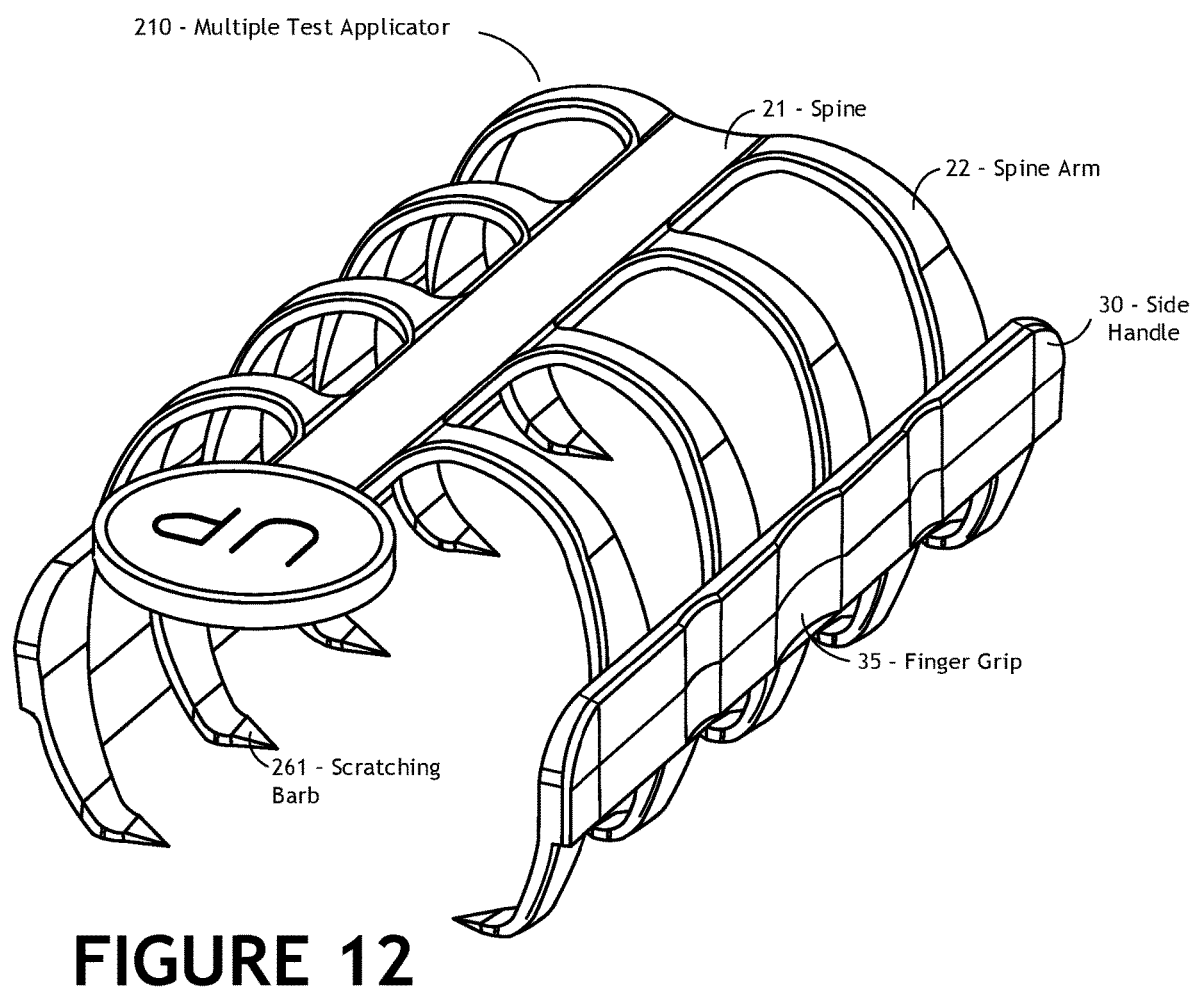
FIG. 12 depicts the first preferred embodiment of the multiple test applicator as shown in FIG. 11.

FIG. 12 depicts the third preferred embodiment of the multiple test applicator [210].

FIGS. 13A, 13B, and 13C depict an alternate embodiment of the method for administering multiple allergens of the present invention, each of the scratching barbs [261] of the multiple test applicator [210] are pointing downward toward the fluid tray [50] when disposed in the fluid tray [50]. The fluid tray [50] contains multiple allergens, generally one allergen [57] in each reservoir [54]. Allergens are initially selected and placed into containment reservoirs [54] in the fluid tray [50], and care is taken not to use an excess amount of the allergens. After allergen loading when the medical technician lifts the multiple test applicator [210] out of the fluid tray [50], the multiple test applicator [10] is in the relaxed state. Using the pair of opposing finger grips [30 and 31], the medical technician applies pressure moving the multiple test applicator [210] to a compressed state before placing the applicator [210] upon the skin of the patient [90] in the allergen deposition position, the medical technician pushes lightly upon the applicator [210] and slowly releases the finger grips [30 and 31]. This generates a scratch [91] at each test site essentially simultaneously on the skin of the patient [90]. Trace amounts of each respective allergen [57] then seep into each respective scratch [91]. The use of the finger grips [30 and 31] to move the multiple test applicator [210] from the relaxed state to the compressed state and then back again to the relaxed state enables one-handed operation by the medical technician. Then, the multiple test applicator [210] is pulled up and away from the skin of the patient [90]. The medical technician then waits between 10 to 20 minutes to determine how the patient has reacted to each of these allergens. After the testing has been completed, the physician analyzes the test results to determine the next course of treatment.

FIG. 13A is a front view of the multiple test applicator [210] in an expanded position, with the scratching barbs [61]. The scratching barbs [61] have been loaded and each include a trace of their respective allergens and are prepared for allergen deposition. FIG. 13B is a front view of the multiple test applicator [210], which is now in a compressed position. The scratching barbs [261] are resting upon the skin of a patient [90] with the each of two scratching barbs [261] pointed downward. FIG. 13C is a front view of the multiple test applicator [210], which is now being in an expanded position. The scratching barbs [61] now have generated a pair of scratches [91] on the skin of the patient [90] at a pair of test sites as the scratching barbs [61] have separated from each other.

Then, the medical technician waits between 10 to 20 minutes to determine how the patient has reacted to these allergens. After the testing has been completed, the physician analyzes the test results to determine the next course of treatment.

Figure 14A:
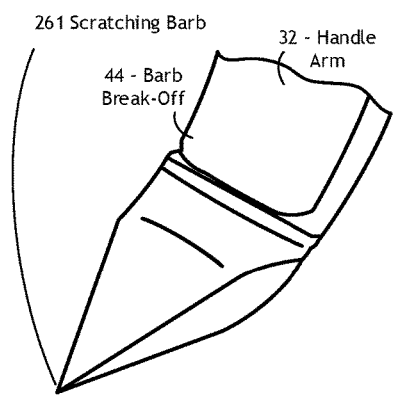
FIG. 14A is an exploded assembly view of the first preferred embodiment of the scratching barb pointed downward away from the spine of the multiple test applicator of FIG. 11, a tip break-off section is also depicted.

FIG. 14A is an exploded assembly view of the first preferred embodiment of the scratching barb [261] pointed downward away from the spine [21] of the multiple test applicator [210]. A barb break-off section [45] also being shown.

Figure 14B:
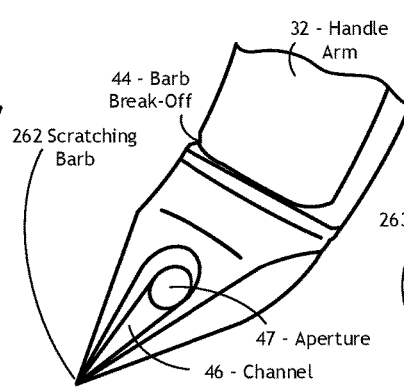
FIG. 14B is an exploded assembly view of a second preferred embodiment of the scratching barb pointed downward away from the spine of the multiple test applicator of FIG. 10, the scratching barb including an aperture and a channel for retaining a trace amount of the allergen, a tip break-off section is also depicted.

FIG. 14B is an exploded assembly view of a second preferred embodiment of the scratching barb [262] pointed downward away from the spine [21] of the multiple test applicator [210], the scratching barb [262] including an aperture [47] and a channel [46] for retaining a trace amount of the allergen [57]. A barb break-off section [45] also being shown.

Figure 14C:
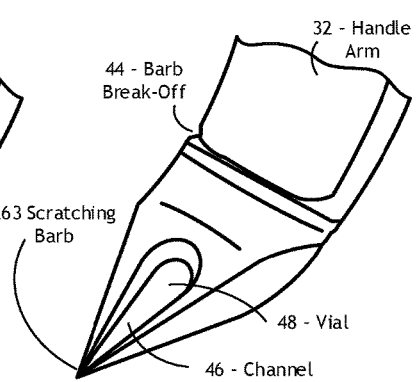
FIG. 14C is an exploded assembly view of a third preferred embodiment of the scratching barb pointed downward away from the spine of the multiple test applicator of FIG. 10, the scratching barb including a vial and a channel for retaining a trace amount of the allergen, a tip break-off section is also depicted.

FIG. 14C is an exploded assembly view of a third preferred embodiment of the scratching barb [263] pointed downward away from the spine [21] of the multiple test applicator [210], the scratching barb [263] including a vial and a channel for retaining a trace amount of the allergen [57], a break-off section also being shown. FIG. 14C depicts the multiple test applicator [110] in the allergen deposition position. A barb break-off section [45] also being shown.

Once allergen loading is complete, the multiple test applicator [10] is removed from the fluid tray [50] and repositioned onto the skin (i.e.—arm, back, or leg) of the patient [90].

In the allergen deposition position, the multiple test applicator [10] is compressed, and each allergen [57] is deposited into each respective scratch [91] generated by each respective scratching barb [61] on the skin of the patient [90] for further analysis as needed by the treating physician.

After the prescribed time between 10 to 20 minutes the test operator records the skin condition with a photo of each scratch site or on a reaction description form. The applicator includes break-off features for the arms, legs, and tips enabling more efficient disposal of the device after use with a patient. The break-off features for the tips enable this part of the applicator to be disposed of in a biohazard sharps container.

The leg break-off points enable the legs to be broken off from the spine and the legs and spine to be disposed of in a separate container from the tips. The testing tray can also be disposed of in the same container or can be reused. This increases the packing density of the discarded material and a much lower disposal cost.

Also, applicator [10] of the multiple allergen testing system has the advantage of breaking the skin of the patient without downward pressure. This diminishes chances of the mast cells (histamine containing cells) releasing the histamine secondary to pressure causing a false positive. This may be a critical factor with percutaneous allergy testing.

The single and multiple allergen testing system [120] enables testing for a single allergy or multiple allergies in the same device. The allergen testing applicator [110] simulates the best practice in a controlled procedure. The multiple-allergen testing system is designed around a multiple allergen testing system [120] that enables the accurate and repeatable placement of allergy testing fluid, either in a tray or on the skin of a patient. The testing procedure also controls the scratching or pricking of the skin, to introduce the allergen in a more controlled manner.

The multiple test applicator [10] and the fluid tray [50] are preferably made of engineering grade polymers that are sterilized prior to use in an autoclave, or other standard sterilization procedures. Hence, the materials preferably are made of plastics that are stable at higher temperatures. The multiple test applicator [10] is depicted having ten scratching barbs. The multiple applicator unit may also have two, four, six, eight, twelve, and any of a wide variety of configurations, as needed.

It is critical during use that the allergens [57] for the various reservoirs [54] do not become intermixed as this contamination will affect the test results. The suggested minimum distance between two neighboring scratching barbs extending from the same side frame is preferably at least three-quarters of an inch.

It is critical that the multiple test applicator unit be held in one hand of the medical technician who is administering the test. This will enable the other hand to be free to take notes, to assist the patient, or do whatever becomes necessary during the administration of the procedure.

Accordingly, the multiple test applicator [10] having ten scratching barbs as depicted is preferably about 2" (height)× 2" (width)×5" (length). If the multiple test applicator has eight scratching barbs (2×4), the length is preferably 3.75" to 4.50" in length, if the multiple test applicator has twelve scratching barbs (2×6), the length is about 5.00 to 5.50", etc. It is to be understood that while the multiple allergen testing device as depicted in the accompanying drawings depicts a unit with ten testing devices, one skilled in the art can readily modify this geometry to include 4, 6, 8, 12, 16, 20, 24, 30, 36, or any other combination of multiple testing devices, this disclosure is being limited to 10 for purposes of illustration only.

Allergens are inserted into containment reservoirs in the loading tray (the trays may also be preloaded). The multiple test applicator [10] is removed from its sterile package. The applicator is removed from the fluid tray [50] and placed onto the skin of the patient [90]. The testing arms are pulled toward the center of the applicator from both sides, raising up the skin of the patient. The pair of skin lifting pads [45] are sandwiched about each scratching barb [61]. The scratching barbs [61] lift the skin and limit the depth of penetration of each scratching barb [61]. From this position, the scratching barb [61] is pulled up and away from the skin of the patient [90]. This action creates a small scratch [91] on the skin of the patient [90] inserting a small amount of allergen [57] under the skin.

The multiple test applicator [10] enables testing for multiple allergies in one device and one test procedure or one test with the single tester and one allergy testing fluid. The most consistent results have been achieved by inserting a drop of allergy testing fluid on the skin and then scratching the skin with a simple needle (best practice referred to as "Lift and Prick"). The multiple test applicator [10] duplicates the best practice but in a controlled, repeatable, and reproducible way. The system built around the devices enables the accurate and repeatable placement of the allergy testing fluid, in a tray and transfers this fluid to the multiple test applicator [10] or the single test applicator [180], by placing the testing end of the device, into the fluid tray [50

The multiple test applicator [10] is removed from the fluid tray [50] and placed on the skin of the patent [90]. The testing arms are pulled toward the center of the multiple allergen testing device from both sides, lifting the skin up. From this position, the applicator [10] is pulled up and away from the skin [90]. This action generates a small scratch [91] on the skin of the patient [90] and moves a trace amount of allergen [57] under the skin of the patient [90].

The scratching barb [61] is subsequently transferred to the skin of the patient [90]. Once the scratching barb [61] of the multiple test applicator [10] is on the skin of the patient, the applicator [10] is moved in such a way, as to lift the skin in front of the scratching barb [61]. The next action is to lift the multiple test applicator [10] perpendicular to the skin of the patient [90], causing the scratching barb [61], which is immersed in allergen [57], to scratch the skin through the dermis and above the epidermis.

After the prescribed time between 10 to 20 minutes the test operator records the skin condition. The Applicator includes break-off features for the arms, legs, and tips enabling more efficient disposal of the device after use with a patient. The break-off features for the tips enable this part of the applicator to be disposed of in a biohazard sharps container. The leg break-off points enable the legs to be broken off from the spine and the legs and spine to be disposed of in a separate container from the tips. The fluid tray [50] can also be disposed of in the same container or can be reused. This increases the packing density of the discarded material and a much lower disposal cost.

Also, the multiple test applicator has the advantage of breaking the skin of the patient without downward pressure. This diminishes chances of the mast cells (histamine containing cells) releasing the histamine secondary to pressure causing a false positive. This may be a critical factor with percutaneous allergy testing.

Throughout this application, various patents and applications are referenced by number and inventor. The disclosures of these documents in their entireties are hereby incorporated by reference into this specification in order to more fully describe the state of the art to which this invention pertains.

It is evident that many alternatives, modifications, and variations of the methods for administering multiple allergens of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10. Multiple Test Applicator—1$^{st}$ Embodiment
20. Multiple Allergen Testing System—1$^{st}$ Embodiment
21. Spine
22. Spine Arm
30. and 31. Side Frame/Handle
32. Handle Arm
35. and 36. Finger Grip
44. Barb Break-Off
45. Skin Lifting Pad
46. Channel
47. Aperture
48. Vial
50. Fluid Tray—1$^{st}$ Embodiment
54. Reservoir
57. Allergen
61. Scratching Barb
62. Scratching Barb
63. Scratching Barb
90. Skin of Patient
91. Scratch
94. Raised Skin
96. Hand of Medical Technician
110. Multiple Test Applicator—2$^{nd}$ Embodiment
120. Multiple Allergen Testing System—2$^{nd}$ Embodiment
180. Single Unit Applicator
210. Multiple Allergen Testing System—3$^{rd}$ Embodiment
220. Multiple Test Applicator—3$^{rd}$ Embodiment
261. Scratching Barb
262. Scratching Barb
263. Scratching Barb

The invention claimed is:

1. A method for administering a plurality of allergens into skin of a patient, said method comprising:
   a. positioning a multiple test applicator during allergen loading onto a fluid tray, said multiple test applicator having first and second scratching barbs, said multiple test applicator being cooperatively engageable with said fluid tray, said fluid tray having a first allergen retainable in a first reservoir, said fluid tray having a second allergen retainable in a second reservoir, said first scratching barb retaining some of said first allergen when removed from said first reservoir, said second scratching barb retaining some of said second allergen when removed from said second reservoir, said multiple test applicator having a relaxed state and a compressed state, said first scratching barb moving away from said second scratching barb when said multiple test applicator changes from said compressed state to said relaxed state, said multiple test applicator being held by one hand of a medical technician during allergen loading; and
   b. relocating said multiple test applicator during allergen deposition onto said skin of said patient, said first scratching barb generating a first scratch onto said skin of said patient as said first allergen is deposited into said first scratch, said second scratching barb generating a second scratch onto said skin of said patient as said second allergen is deposited into said second scratch, said multiple test applicator being held by one hand of said medical technician during allergen deposition.

2. The method of claim 1, wherein first scratching barb moves away from said second scratching barb as said first scratch and said second scratch are formed.

3. The method of claim 2, wherein said multiple test applicator includes a first side frame member and a second side frame member, said first side frame member opposing said second side frame member, pressing said first side frame member to said second side frame member facilitating a repositioning of said multiple test applicator from said relaxed state to said compressed state.

4. The method of claim 1, wherein said first scratching barb opposes said second scratching barb, said first scratching barb moving toward said second scratching barb when said multiple test applicator changes from said relaxed state to said compressed state.

5. The method of claim 1, wherein said first and second scratching barbs project upward when disposed in said fluid tray.

6. The method of claim 1, wherein said first and second scratching barbs project upward when disposed in said fluid tray, said first scratching barb being sandwiched between a pair of skin lifting pads.

7. The method of claim 1, wherein said first scratching barb opposes said second scratching barb, said multiple test applicator being in said relaxed state during allergen loading, said first scratching barb moving toward said second scratching barb when said multiple test applicator is repositioned into said compressed state.

8. A method for administering a plurality of allergens into skin of a patient, said method comprising:
   a. positioning a multiple test applicator during allergen loading onto a fluid tray, said multiple test applicator being cooperatively engageable with said fluid tray, said multiple test applicator including a first and second scratching barb, said multiple test applicator having a first side frame, said multiple test applicator having a second side frame, said first side frame opposing said second side frame, said multiple test applicator including a first finger grip disposed on said first side frame, said multiple test applicator including a second finger grip disposed on said second side frame, said fluid tray having a first allergen retainable in a first reservoir, said first scratching barb retaining some of said first allergen when removed from a first reservoir, said fluid tray having a second allergen retainable in said second reservoir, said first scratching barb retaining some of said first allergen when removed from said first reservoir during allergen loading, said second scratching barb retaining some of said second allergen when removed from said second reservoir during allergen loading, said multiple test applicator having a relaxed state and a compressed state, said multiple test applicator being in said relaxed state during allergen loading, said first scratching barb moving toward said second scratching barb when said multiple test applicator repositions into said compressed state; and b. relocating said multiple test applicator during allergen deposition onto said skin of said patient, said first scratching barb generating a first scratch onto said skin of said patient as said some of said first allergen is deposited into said first scratch, said second scratching barb generating a second scratch onto said skin of said patient as said some of said second allergen is deposited into said second scratch, said multiple test applicator scratching said skin of said patient without applying downward pressure.

9. The method of claim 8, wherein said first scratching barb moves away from said second scratching barb as said first scratch and said second scratch are formed.

10. The method of claim 8, wherein said first scratching barb opposes said second scratching barb, said first scratching barb moving toward said second scratching barb when said multiple test applicator changes from said relaxed state to said compressed state.

11. The method of claim 8, wherein said multiple test applicator includes a first side frame member and a second side frame member, said first side frame member opposing said second side frame member, compressing said first side frame member to said second side frame member facilitating a repositioning of said multiple test applicator from said relaxed state to said compressed state.

12. The method of claim 8, wherein said first and second scratching barbs project upward when disposed in said fluid tray.

13. The method of claim 8, wherein said first and second scratching barbs project upward when disposed in said fluid tray, said first scratching barb being sandwiched between a pair of skin lifting pads.

14. The method of claim 8, wherein said multiple test applicator includes a first side frame member and a second side frame member, said first side frame member opposing said second side frame member, a first finger grip being disposed on said first side frame member, a second finger grip being disposed on said second side frame member, said first and second finger grips facilitating a repositioning of said multiple test applicator from said compressed state to said relaxed state.

15. A method for administering a plurality of allergens into skin of a patient, said method comprising:

a. positioning a multiple test applicator during allergen loading onto a fluid tray, said multiple test applicator having a first scratching barb positionable on a first applicator leg, said multiple test applicator having a second scratching barb positionable on a second applicator leg, said first scratching barb of said multiple test applicator being cooperatively engageable with a first reservoir of said fluid tray during allergen loading, said second scratching barb of said multiple test applicator being cooperatively engageable with a second reservoir of said fluid tray, said fluid tray having a first allergen retainable in said first reservoir, said fluid tray having a second allergen retainable in said second reservoir, said first scratching barb retaining some of said first allergen when removed from said first reservoir during allergen loading, said second scratching barb retaining some of said second allergen when removed from said second reservoir during allergen loading, said first scratching barb projecting upwards when positioned in said fluid tray, said second scratching barb projecting upwards when positioned in said fluid tray; and b. relocating said multiple test applicator from said fluid tray onto said skin of said patient during allergen deposition, said first scratching barb generating a first scratch onto said skin of said patient as said first allergen is deposited from said first scratching barb into said first scratch while said second scratching barb generates a second scratch onto said skin of said patient as said second allergen is deposited from said second scratching barb into said second scratch.

16. The method of claim 15, wherein said first scratching barb opposes said second scratching barb, said multiple test applicator having a relaxed state and a compressed state, said first scratching barb moving toward said second scratching barb when said multiple test applicator moves into said compressed state.

17. The method of claim 15, wherein said multiple test applicator has a relaxed state and a compressed state, said first scratching barb moving toward said second scratching barb when said multiple test applicator repositions into said compressed state, said first scratching barb contacts a first test site of a raised portion of said skin of said patient when said multiple test applicator is in said compressed state while said second scratching barb contacts a second test site of a raised portion of said skin of said patient.

18. The method of claim 15, wherein said first scratching barb being sandwiched between a pair of skin lifting pads.

19. The method of claim 15, wherein said first allergen is deposited into said first scratch as said second allergen is deposited into said second scratch.

20. The method of claim 15, further comprising said multiple test applicator including a first finger grip disposed on a first side frame member, and said multiple test applicator including a second finger grip disposed on a second side frame member, said multiple test applicator having a relaxed state and a compressed state, wherein pressure is applied through said first and said second finger grips as said multiple test applicator is moved from said relaxed state to said compressed state as said first scratching barb generates said first scratch and said second scratching barb generates said second scratch on said skin of said patient.

21. The method of claim 15, wherein said first scratch and said second scratch are not generated by needle pricks.

22. A method for administering a plurality of allergens into skin of a patient, said method comprising:

a. positioning a multiple test applicator during allergen loading onto a fluid tray, said a multiple test applicator having a first scratching barb disposed on a first applicator leg, said multiple test applicator having a second scratching barb disposed on a second applicator leg, said first scratching barb opposing said second scratching barb, said first scratching barb of said multiple test applicator being cooperatively engageable with a first reservoir of said fluid tray during allergen loading, said second scratching barb of said multiple test applicator being cooperatively engageable with second reservoir of said fluid tray, said fluid tray having a first allergen retainable in said first reservoir, said fluid tray having a second allergen retainable in said second reservoir, said first scratching barb retaining some of said first allergen when removed from said first reservoir during allergen loading, said second scratching barb retaining some of said second allergen when removed from said second reservoir during allergen loading, said first and said second scratching barbs pointing downward toward said loading tray, said multiple test applicator having a relaxed state and a compressed state, said multiple test applicator being in said relaxed state during allergen loading;

b. removing said multiple test applicator from said fluid tray, repositioning said multiple test applicator from said relaxed state to said compressed state prior to placing said multiple test applicator on said skin of said patient; and c. relocating said multiple test applicator from said fluid tray onto said skin of said patient during allergen deposition, where said first scratching barb generates a first scratch onto said skin of said patient as a portion of said first allergen is deposited from said first scratching barb into said first scratch while said second scratching barb generates a second scratch onto said skin of said patient as a portion of said second allergen is deposited from said second scratching barb into said second scratch, said first scratching barb moving away from said second scratching barb as said first scratch and said second scratch are formed.

23. The method of claim 22, wherein said multiple test applicator includes a first side frame member and a second side frame member, said first side frame member opposing said second side frame member, pressing said first side frame member to said second side frame member facilitating a repositioning of said multiple test applicator from said relaxed state to said compressed state, releasing said pressure between said first and second frame member facilitating a repositioning of said multiple test applicator from said compressed state to said relaxed state.

24. The method of claim 22, wherein said multiple test applicator includes a first side frame member and a second side frame member, said first side frame member opposing said second side frame member, compressing said first side frame member to said second side frame member facilitating a repositioning of said multiple test applicator from said relaxed state to said compressed state.

25. The method of claim 22, wherein said multiple test applicator includes a first side frame member and a second side frame member, said first side frame member opposing said second side frame member, releasing compression of said first side frame member against said second side frame member facilitating a repositioning of said multiple test applicator from said compressed state to said relaxed state.

26. The method of claim 22, wherein said first scratching barb moves nearer to said second scratching barb when said multiple test applicator changes from said relaxed state to said compressed state.

27. The method of claim 22, wherein said first scratching barb moves nearer to said second scratching barb when said multiple test applicator changes from said relaxed state to said compressed state and said first scratching barb moves away from said second scratching barb when said multiple test applicator changes from said compressed state to said relaxed state.

28. The method of claim 22, wherein said first scratching barb moves away from said second scratching barb when said multiple test applicator changes from said compressed state to said relaxed state.

* * * * *